United States Patent [19]

Klein et al.

[11] 4,171,326

[45] * Oct. 16, 1979

[54] PROCESS FOR PREPARING 2-(1-CYCLOHEXENYL)-CYCLOHEXANONE

[75] Inventors: Joseph F. M. Klein, Bunde; Petrus A. M. J. Stijfs, Munstergeleen; Jozef A. Thoma, Sittard, all of Netherlands

[73] Assignee: Stamicarbon, B.V., Geleen, Netherlands

[*] Notice: The portion of the term of this patent subsequent to Oct. 4, 1994, has been disclaimed.

[21] Appl. No.: 810,374

[22] Filed: Jun. 27, 1977

Related U.S. Application Data

[63] Continuation-in-part of Ser. No. 649,575, Jan. 16, 1976, Pat. No. 4,052,458.

[30] Foreign Application Priority Data

Jan. 17, 1975 [NL] Netherlands ............... 7500549

[51] Int. Cl.$^2$ ............................................. C07C 45/00
[52] U.S. Cl. ................................................ 260/586 C
[58] Field of Search ................................... 260/586 C

[56] References Cited

U.S. PATENT DOCUMENTS

| 3,880,930 | 4/1975 | Ramm et al. ............... 260/586 C |
| 4,052,458 | 10/1977 | Klem et al. ............... 260/586 C |

FOREIGN PATENT DOCUMENTS 51-4556 7/1976 Japan.

*Primary Examiner*—Norman Morgenstern
*Attorney, Agent, or Firm*—Cushman, Darby & Cushman

[57] ABSTRACT

2-(1-cyclohexyl)-cyclohexanone is prepared by condensation of cyclohexanone using a macro-porous ion exchange resin such as Lewatite SPC 118 W or equivalent at temperatures not exceeding 125° C., provided that the conversion reaction is maintained below 50%, preferably below 35%. The reaction mixture is distilled at atmospheric pressure in the absence of the ion exchange resin and the desired product is recovered in substantially high yields generally greater than 95%.

9 Claims, No Drawings

PROCESS FOR PREPARING 2-(1-CYCLOHEXENYL)-CYCLOHEXANONE

This is a continuation-in-part of our prior application Ser. No. 649,575 filed Jan. 16, 1976 and now U.S. Pat. No. 4,052,458, issued Oct. 4, 1977.

BACKGROUND OF THE INVENTION

This invention relates to a process for preparing 2-(1-cyclohexenyl)-cyclohexanone (abbreviated and referred to hereinafter as CHNA) by condensation of a cyclohexanone. CHNA so produced can be dehydrogenized to ortho-phenyl-phenol, which is useful as a preservative.

The preparation of CHNA has been described in various patents and publications. According to German patent specification No. 857,960 CHNA can be obtained by passing cyclohexanone through an acid ion exchanger at 90° C. and subjecting the resulting liquid to distillation under reduced pressure. Using this procedure the yields amount to only 80% of the yield theoretically possible, while a relatively large quantity of ion exchanger is needed. In Compt. rend. 236, 1571 (1953) Durr states that the condensation of cyclohexanone to CHNA at a temperature of 130°-140° C. takes place with only a very low yield, that is 20%, if the commercially available ion exchanger known as Amberlite IR-120 is used. Contrary to Durr's publication, Japanese Patent Publication No. 70-41,377 mentions for the relevant conversion using the same ion exchange resin Amberlite IR-120 and a temperature of 130°-135° C., a yield of 97.5% is obtained. French patent specification No. 2,186,456 in turn mentions as a substantial disadvantage of the process according to the Japanese Patent Publication that the optimum temperature range of 130°-135° C. mentioned in that publication is in fact higher than the maximum permissible working temperature of most cation exchangers, which in practice results in high production costs.

According to this French Patent publication the desired conversion is better accomplished using a lower temperature of 80°-110° C., a pressure of 60-200 millimeter Hg and, during the conversion, by separating off the water formed by evaporation. From the reaction mixture obtained the required product is then recovered by distillation under reduced pressure. A readily apparent disadvantage of this process is the required use of reduced pressure, which on a commercial scale is costly to install and operate. Even using the reduced pressure technique the yield achieved is no greater than approximately 90%.

DETAILED DESCRIPTION OF THE INVENTION

The present invention provides a particularly suitable process for preparation of CHNA. The process according to the present invention for preparing CHNA by condensation of cyclohexanone in the presence of a strong acid ion exchanger as a catalyst and removal of water formed by distillation of the resulting reaction mixture, is characterized in that the condensation of cyclohexanone is carried out using a macro-porous ion exchanger at atmospheric pressure and a temperature between about 50° C. and about 125° C. Conversion of the cyclohexanone is not permitted to rise above about 50%. The resulting reaction mixture is then distilled in the absence of the ion exchanger.

As used herein, the macro-porous ion exchanger is an ion exchanger or ion exchange resin system which consists of the sulfonated copolymer of sytrene with about 15 to 20% by weight of divinyl benzene and with pores whose average size exceeds 100 Ångstrom in diameter and/or having an internal surface area larger than 30 m$^2$ per gram.

Distillation of the reaction product obtained according to the invention is conveniently conducted at atmospheric pressure.

In the process according to the present invention the desired product can be recovered, without the use of reduced pressure, in a substantially high yield and at low catalyst costs.

The condensation according to the present invention is preferably conducted at a temperature between about 75° and about 115° C. The conversion of the cyclohexanone is preferably kept below about 35%. The lower limit of the conversion may depend on reaction conditions, reactants, the nature of the catalyst and the like, and are preferably maintained fairly low, such as about 5%, although sometimes the percent conversion may be as low as 1.9% or even lower, without detracting from the high yields obtained for the overall process.

Various macro-porous acid ion exchangers may be used in the process of the invention and examples of suitable ion exchange resins are resins commercially available under the names of: Amberlite 200, Amberlist 15, Dowex MSC 1, Lewatite SPC 118 W, Imac C 16 P, and Realite CFZ. Other ion exchange resins having the indicated properties may also be used.

The process according to the invention is practiced by passing the cyclohexanone through the ion exchanger, for instance at a space velocity of between 1 and 659 grams of cyclohexanone per gram of dry ion exchanger per hour.

The process according to the present invention will be further illustrated in the following working examples. All parts and percentages are by weight unless otherwise indicated.

EXAMPLE 1

At different temperatures and space velocities, cyclohexanone was continuously pumped through a glass tubular reactor, which contained the catalyst. The reactor was provided with a heating jacket through which a heating medium flowed. The tube had a length of 25 cm and an internal diameter of 20 mm. The reaction mixture obtained was passed to a distillation device, where the reaction water was removed as an azeotrope with cyclohexanone by distillation at atmospheric pressure. The mixture of cyclohexanone and water then obtained was separated and the cyclohexanone recycled; the residue, which consisted mainly of 2-(1-cyclohexenyl)-cyclohexanone and cyclohexanone, was discharged. If desired, this residue may be further separated into its components by distillation and the desired product recovered. The conversions and the yields reported in the following tables and examples relate to the reaction mixture as it left the catalyst and represent averages calculated for the entire duration of the test.

The yield is calculated as follows:

$$\frac{\text{moles of } CHNA \text{ formed}}{\text{moles of cyclohexanone converted}} \times \tfrac{1}{2} \times 100\%$$

The space velocity (s.v.) is expressed in grams of cyclohexanone per gram of dry catalyst per hour. Lewatite SP 120 in the H+ form was used as the catalyst.

| Test No. | Catalyst Temperature °C. | S.V. | Test Duration Hours | Conversion % | Yield % |
|---|---|---|---|---|---|
| 1-1 | 110 | 660 | 4 | 6.8 | 95.2 |
| 1-2 | 110 | 1320 | 22 | 4.2 | 95.4 |
| 1-3 | 100 | 1320 | 7 | 3.6 | 95.6 |
| 1-4 | 90 | 1320 | 7 | 2.2 | 97.3 |
| 1-5 | 80 | 214 | 7 | 4.4 | 98.0 |
| 1-6 | 90 | 5 | 12 | 30 | 97.0 |

EXAMPLE 2

In the same manner as Example No. 1, additional tests were conducted using Amberlite-200 in the H+ form as the catalyst.

The results of this series are given in the following table.

| Test No. | Catalyst Temperature °C. | S.V. | Test Duration Hours | Conversion % | Yield % |
|---|---|---|---|---|---|
| 2-1 | 100 | 1320 | 7 | 3.6 | 95.4 |
| 2-2 | 90 | 1320 | 7 | 2.2 | 97.1 |
| 2-3 | 80 | 214 | 7 | 4.4 | 98.0 |

EXAMPLE 3

In the same manner as in Example 1, additional tests were conducted using Amberlist 15 in the H+ form as the catalyst.

The results are given in the following table.

| Test No. | Catalyst Temperature °C. | S.V. | Test Duration Hours | Conversion % | Yield % |
|---|---|---|---|---|---|
| 3-1 | 100 | 1320 | 7 | 3.6 | 95.6 |
| 3-2 | 90 | 1320 | 7 | 2.2 | 97.2 |
| 3-3 | 80 | 214 | 7 | 4.4 | 97.9 |

EXAMPLE 4

In the same manner as Example 1, additional experiments using Realite CFZ in the H+ form as the catalyst. The results are given in the following table.

| Test No. | Catalyst Temperature °C. | S.V. | Test Duration Hours | Conversion % | Yield % |
|---|---|---|---|---|---|
| 4-1 | 100 | 1320 | 7 | 3.1 | 95.8 |
| 4-2 | 90 | 1320 | 7 | 1.9 | 97.5 |
| 4-3 | 80 | 214 | 7 | 3.8 | 98.2 |

These experiments demonstrate that substantially the same high yields are obtained using various specific commercially available catalysts.

EXAMPLE 5

In the same manner as Example No. 1, additional tests were conducted using Lewatite SPC 118 W in the H+ form as the catalyst.

the results are given in the following table.

| Test no. | Catalyst temperature °C. | S.V. | Test, duration Hours | Conversion % | Yield % |
|---|---|---|---|---|---|
| 5-1 | 86 | 4.13 | 24 | 27.6 | 97.9 |
| 5-2 | 82 | 8 | 24 | 18.0 | 97.3 |
| 5-3 | 83 | 16 | 24 | 18.8 | 98.0 |
| 5-4 | 92 | 6 | 24 | 25.8 | 99.6 |
| 5-5 | 93 | 16 | 24 | 19.9 | 97.0 |
| 5-6 | 91 | 24 | 24 | 18.4 | 97.9 |
| 5-7 | 91 | 32 | 24 | 15.4 | 95.0 |
| 5-8 | 92 | 64 | 24 | 12.1 | 97.8 |
| 5-9 | 101 | 16 | 24 | 22.1 | 98.0 |
| 5-10 | 105 | 24 | 24 | 22.3 | 97.4 |
| 5-11 | 100 | 16 | 24 | 21.4 | 97.0 |
| 5-12 | 112 | 16 | 24 | 26.3 | 97.0 |
| 5-13 | 110 | 24 | 24 | 22.4 | 96.5 |
| 5-14 | 100 | 8 | 120 | 21.0 | 96.0 |
| 5-15 | 100 | 8 | 288 | 21.0 | 98.0 |
| 5-16 | 100 | 8 | 456 | 21.0 | 96.0 |
| 5-17 | 100 | 8 | 528 | 20.0 | 98.0 |

COMPARATIVE EXAMPLE

Cyclohexanone (600 g) and dry Amberlite-200 in the H+ (20 g) form were transferred to a flask equipped with a stirrer and a reflux cooler with water separator; the contents of the flask were heated with stirring. At a temperature of 95° C. the cyclohexanone-water azeotrope started to boil. Heating was then continued for one more hour, during which the temperature of the reaction mixture of the flask rose to 142° C. During the boiling with return of cyclohexanone, 46.5 g of water collected in the water separator. Next the catalyst was filtered off and the filtrate subjected to fractional distillation at a reduced pressure. 214 g of cyclohexanone, 246 g of 2-(1-cyclohexenyl)-cyclohexanone, and 93 g of high-boiling produce were then obtained. The cyclohexanone conversion amounted to 64.3% and the 2-(1-cyclohexenyl)-cyclohexanone yield to 70.2%.

What is claimed is:

1. In a process for preparing 2-(1-cyclohexenyl)cyclohexanone including condensing cyclohexanone in the presence of a strong acid ion exchange catalyst and removing the water formed by distillation of the resulting reaction mixture, the improvement comprising conducting the condensation with a macro-porous ion exchange resin at atmospheric pressure and a temperature of about 50° to 125° C., the macro-porous ion exchange resin comprising a sulfonated copolymer of styrene having 15 to 20% by weight of divinyl benzene therein, and pores having an average pore size in excess of 100 Å in diameter, or an internal surface area greater than 30 square meters per gram, or both, contacting the cyclohexanone with the macro-porous ion exchange resin at a space velocity from 1 to 659 grams of cyclohexanone per gram of resin per hour, continuing the condensation such that the conversion of the cyclohexanone is maintained at 50% or less, separating the ion exchange resin from the reaction mixture and distilling the reaction mixture to remove the water formed in the absence of the ion exchange resin and recovering the 2-(1-cyclohexenyl)-cyclohexanone product.

2. The process according to claim 1 wherein the distillation of the reaction mixture is conducted at atmospheric pressure.

3. The process according to claim 1 wherein the condensation is conducted at a temperature of about 75° to 115° C.

4. The process according to claim 1 wherein the conversion of the cyclohexanone is maintained no greater than 35%.

5. The process according to claim 1 wherein the cyclohexanone is contacted with the macro-porous ion exchange resin at a space velocity of from 4 to 659 grams of cyclohexanone per gram of resin per hour.

6. The process according to claim 5 wherein the space velocity ranges from 4 to 100 grams of cyclohexanone per gram of resin per hour.

7. The process according to claim 5 wherein the space velocity ranges from 4 to 64 grams of cyclohexanone per gram of resin per hour.

8. The process according to claim 5 wherein the space velocity ranges from 4 to 214 grams of cyclohexanone per gram of resin per hour.

9. The process according to claim 5 wherein the space velocity ranges from 214 to 659 grams of cyclohexanone per gram of resin per hour.

* * * * *